US012667540B2

(12) United States Patent
Müller et al.

(10) Patent No.: US 12,667,540 B2
(45) Date of Patent: Jun. 30, 2026

(54) ROLLED ORAL THIN FILMS HAVING A HIGH LEVEL OF ACTIVE-INGREDIENT LOADING

(71) Applicant: LTS LOHMANN THERAPIE-SYSTEME AG, Andernach (DE)

(72) Inventors: Markus Müller, Troisdorf (DE); Christoph Schmitz, Rheinbrohl (DE); Michael Linn, Waldböckelheim (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 451 days.

(21) Appl. No.: 18/282,365

(22) PCT Filed: Mar. 17, 2022

(86) PCT No.: PCT/EP2022/057068
§ 371 (c)(1),
(2) Date: Sep. 15, 2023

(87) PCT Pub. No.: WO2022/195044
PCT Pub. Date: Sep. 22, 2022

(65) Prior Publication Data
US 2024/0156727 A1      May 16, 2024

(30) Foreign Application Priority Data
Mar. 17, 2021      (DE) .......................... 102021106491.0

(51) Int. Cl.
*A61K 9/00* (2006.01)
*A61K 45/06* (2006.01)
(Continued)

(52) U.S. Cl.
CPC .............. *A61K 9/006* (2013.01); *A61K 45/06* (2013.01); *A61K 47/10* (2013.01); *A61K 47/22* (2013.01); *A61K 47/26* (2013.01); *A61K 47/32* (2013.01)

(58) Field of Classification Search
CPC ........ A61K 31/00; A61K 45/06; A61K 47/10; A61K 47/22; A61K 47/26; A61K 47/32; A61K 9/006; A61K 9/7007
See application file for complete search history.

(56) References Cited

U.S. PATENT DOCUMENTS 3,625,214 A      12/1971      Higuchi
7,615,235 B2      11/2009      Rademacher et al.
(Continued)

FOREIGN PATENT DOCUMENTS

DE          19715794 C1      12/1998
DE          19946822 A1      4/2001
(Continued)

OTHER PUBLICATIONS

Muller et al. WO 2018/224591, English translation (Year: 2018).*
(Continued)

*Primary Examiner* — Savitha M Rao
(74) *Attorney, Agent, or Firm* — Lippes Mathias LLP

(57) ABSTRACT

The present invention relates to a method for producing a water-erodible, water-soluble or water-dispersible active-ingredient-administering form, in which, firstly, a film suitable as an oral film-administering form is produced which contains the active ingredient and in which a surface of the film is activated in a subsequent step in order to generate a tacky surface, followed by rolling up the activated film to form a rolled-up laminate. The present invention also relates to rolled-up laminates produced according to this method. Corresponding laminates are very stable, such that they can (Continued)

Figure 1:
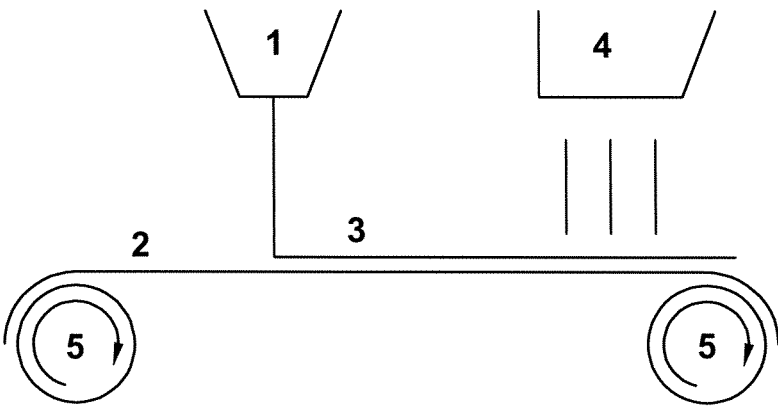

be dispensed and cut, and are suitable on account of their area density, which is very high by comparison with conventional OTF products, for administering active ingredients which have to be given in larger amounts.

18 Claims, 2 Drawing Sheets

(51) Int. Cl.

| | |
|---|---|
| *A61K 47/10* | (2017.01) |
| *A61K 47/22* | (2006.01) |
| *A61K 47/26* | (2006.01) |
| *A61K 47/32* | (2006.01) |

(56) References Cited

U.S. PATENT DOCUMENTS

| | | | |
|---|---|---|---|
| 9,205,049 | B2 | 12/2015 | Reddy et al. |
| 2008/0241216 | A1 | 10/2008 | Von Falkenhausen et al. |
| 2010/0119583 | A1 | 5/2010 | Rosenberg et al. |
| 2014/0107227 | A1 | 4/2014 | Masters et al. |
| 2020/0138714 | A1 | 5/2020 | Muller et al. |
| 2020/0289402 | A1 | 9/2020 | Schmitz et al. |

FOREIGN PATENT DOCUMENTS

| | | | |
|---|---|---|---|
| JP | 10-287589 | A | 10/1998 |
| JP | 2003-510270 | A | 3/2003 |
| JP | 2005-517722 | A | 6/2005 |
| JP | 2007-70344 | A | 3/2007 |
| JP | 2009-507854 | A | 2/2009 |
| JP | 2012-528789 | A | 11/2012 |
| JP | 2020-530433 | A | 10/2020 |
| JP | 2021-504318 | A | 2/2021 |
| WO | 2006114604 | A2 | 4/2006 |
| WO | 2018224591 | A1 | 12/2018 |

OTHER PUBLICATIONS

International Search Report for PCT/EP2022/057068, dated Jul. 6, 2022, 6 pages.

Office Action for German Application No. 102021106491.0, dated Dec. 10, 2021, 8 pages.

Office Action for Japanese Patent No. 2023-556963, mailed Mar. 11, 2025, 10 pages.

\* cited by examiner

ROLLED ORAL THIN FILMS HAVING A HIGH LEVEL OF ACTIVE-INGREDIENT LOADING

The present invention relates to a method for producing rolled-up oral thin film laminates, and also to rolled-up laminates produced in accordance with the method.

PRIOR ART

Oral thin films, also referred to as transmucosal administration systems, are thin active-ingredient-containing polymer-based films which, when applied to a mucous membrane, especially the oral mucosa, deliver the active ingredient directly into same. These dosage systems have the advantage that the active ingredient is absorbed for the most part by the mucous membrane, thus avoiding the first-pass effect, which must be considered in the case of the conventional dosage form of an active ingredient in tablet form.

One difficulty in the production of oral thin films is encountered in practice when attempting to produce films having high area densities. In order to provide high area densities, it is necessary on the one hand to produce the film provided for drying as a comparatively thick film, which leads to problems in the drying process. Alternatively, films having high area densities can also be produced by applying a plurality of layers to one another, layer by layer, with drying steps in between, however, this does not lead in all cases to a film product of satisfactory structural integrity. In addition, when constructing oral thin films layer by layer, multiple application and drying steps are necessary, which makes the production of such films relatively complicated.

If larger amounts of active ingredient are to be administered by means of an oral thin film, there is additionally the problem that only limited space is available at the application site, for example on the palate or in the cheek, and therefore the size of the film product is limited by these basic conditions.

DE 199 46 822 A1 discloses an active-ingredient-containing and/or excipient-containing preparation for controllable release of these substances in respect of time and/or dose, comprising at least two layers in rolled or folded form. Here, the first of these layers, which contains the at least one active ingredient or excipient, is constructed such that at least one of the parameters constituted by thickness of the layer, width of the layer, and concentration of the active ingredient is not constant in this layer.

Against this background, there is a need for administration forms for active pharmaceutical ingredients and other substances that are administered in larger amount. The administration forms should provide the advantages of an application system on the basis of a rapidly dissolving dosage form, such as an oral thin film, and additionally should transport the greatest possible active ingredient amount whilst retaining relatively small external dimensions. When producing the administration forms, the known problems of oral thin films with high area density should be avoided.

The present invention addresses this need.

DESCRIPTION OF THE INVENTION

It has been found that rolled laminates of films that are based on the same materials as conventional oral thin films can transport a high active ingredient content in a limited volume and can be formulated with a high total weight. Such rolled laminates can be placed easily into the cheek pouch or next to or beneath the tongue, and can release the active ingredient there.

Consequently, a first aspect of the present invention relates to a method for producing a water-erodible, water-soluble or water-dispersible active-ingredient-administering form, comprising the steps of (a) producing a film, suitable as oral film-administering form, having a content of active ingredient, (b) activating a surface of the film produced in (a) in order to generate a tacky surface, and (c) rolling up the film activated in (b) to form a rolled-up laminate.

Within the scope of this method it is expedient if the tacky surface generated in (b) is positioned in step (c) such that the tacky side is located on the inner side, so that no tacky residues remain on the outer side in the finished, rolled-up laminate.

The film is produced in (a) usually by applying a free-flowing mass of the composition, which subsequently forms the film, and drying the mass so as to form the film. A suitable device for producing corresponding films is shown schematically in FIG. 1. The free-flowing mass is applied via a suitable unit 1 to a substrate strip 2, wherein a film 3 forms on the substrate strip. By movement, for example by corresponding drive rolls 5, the film is then guided into a dryer 4 and is dried there to form a solidified film. After the drying, the film can be separated from the substrate strip 2.

In a preferred embodiment of the method according to the invention, the surface is activated and a tacky surface generated in (b) by etching the surface. For etching, for example a small amount of a suitable solvent, such as water or a pharmaceutically acceptable alcohol, for example ethanol, can act in vapour form on the surface of the film or can be applied in liquid form, whereby the film swells or is dissolved to a limited extent in the region close to the surface. With the film swollen or dissolved in this way to a limited extent, by rolling up the film a composite can then be produced between the activated (first) surface and the non-activated (second) surface of the rolled-up film. The advantage of the swelling in comparison to the etching lies in the fact that the film remains coherent during this step. After the rolling up, the small amount of water or pharmaceutically acceptable alcohol used to swell/etch the surface of the film can spread by diffusion in the rolled-up film and/or can be removed therefrom by drying. Because in this kind of activation no intermediate layer is created, the rolled-up laminate consists exclusively of the material forming the film.

In a further preferred embodiment of the method according to the invention, the surface is activated and a tacky surface is generated in (b) by melting the surface, for example by heating the surface and partially liquefying it by means of a suitable heating device.

In an alternative preferred embodiment, the surface is activated and a tacky surface is generated in (b) by applying a self-adhering layer, wherein the self-adhering layer is formed from a water-erodible material and preferably a water-soluble or water-dispersible material. A water-soluble material is preferred for the self-adhering layer.

Such a self-adhering layer is produced, for example, by dissolving a water-soluble and/or water-dispersible material in water and/or a pharmaceutically acceptable solvent, preferably an alcohol, such as ethanol, and spreading this in a thin layer on a (dehesively finished) carrier film. This layer is dried to a residual water content or a residual solvent content, which gives this layer a certain tackiness. In this state, this layer is now applied to the (first) surface of the film produced in step (a), wherein the carrier film can be removed. This makes it possible for the "self-adhering layer" to have a very small layer thickness of from 1 to 100 μm, especially 2 to 20, and especially preferably 4 to 10 μm. Here too, the residual water or residual solvent content in the rolled-up laminate can spread by diffusion or can be reduced by drying.

This type of activation of the (first) surface of the film and finishing with a tacky surface is advantageous especially when using a foam-like film in step (a). The risk of a swelling or etching of the film is largely ruled out, and therefore the foam structure of the film is not impaired. The (dried) material of the adhesive layer remains in the rolled-up laminate between the "activated" and the "non-activated" surface of the film.

The application of a self-adhering layer can be assisted by pressing the self-adhering layer lightly against the active-ingredient-containing layer, for example with the aid of a rubber roll. When applying self-adhering layers, the pressing force must be set suitably, so that for example an active-ingredient-containing foam film is not damaged by the pressing. A person skilled in the art can determine a sensible pressing force here by suitable tests known to them.

A third type of activation of the (first) surface of the film lies in its melting. For this purpose, energy (for example in the form of heat) is applied to this surface so that—especially when using a foam-like film—this surface is softened, which leads, after rolling up and then cooling of the rolled-up laminate, to a permanent bonding of the (first) surface thus activated to the (second) surface not activated.

Rolled-up laminates produced according to the method described above can then be cut to a suitable length as necessary and packaged in the usual way, for example by means of a tubular bag machine.

With regard to the film suitable as an oral film-administering form, the present invention is not subject to any relevant limitations, on the proviso that the film is suitable in principle as an oral film-administering form, i.e., that it dissolves relatively quickly upon contact with saliva and disintegrates so that the excipient or active ingredient contained in the film is released. The constituents contained in the film should additionally be pharmaceutically acceptable. Inter alia, water-soluble polymers that are pharmaceutically acceptable are examples of suitable film-forming materials. Especially suitable water-soluble polymers are, for example, starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohol, polyethylene oxide polymers, polyacrylamides, polyethylene glycol, gelatines, collagen, alginates, pectins, pullulan, tragacanth, chitosan, alginic acid, arabinogalactan, galactomannan, agar, agarose, carrageenan, and natural gums. Especially preferred in the context of the present invention are water-soluble polymers that are selected from the group comprising polyvinyl alcohol, polyethylene glycol, polyethylene oxide, cellulose derivatives, pullulan, gelatines, and agar. Most preferred in the context of the present invention is polyvinyl alcohol as water-soluble polymer.

The proportion of the film-forming polymer in the film, which is suitable as an oral film-administering form, is preferably 25 to 85 wt. %, preferably 50 to 85 wt. %, and more preferably 60 to 80 wt. %. In some cases, if this does not adversely affect the integrity of the film, the polymer content in the film may also lie in the lower range, for example in the range of from 25 to 50 wt. %, or preferably in the range of 38 to 40 wt. %.

The active ingredient can be, in principle, any orally administerable active ingredient, wherein active pharmaceutical ingredients are preferred. Active pharmaceutical ingredients that are suitable in the context of the present invention for oral applications are, for example, antiallergics, antiarrhythmics, antibiotics, antidiabetics, antiepileptics, antihistamines, antitussives, cardiotonics, diuretics, hypotensives, expectorants, nerve-muscle blockers, sexual hormones, and vasopressors. Specific examples are acetaminophen, adrenaline, alprazolam, amlodipine, anastrozole, apomorphine, aripiprazole, atorvastatin, baclofen, benzocaine, benzocaine/menthol, benzydamine, buprenorphine, buprenorphine/naloxone, buprenorphine/naloxone/cetirizine, cetirizine, chlorpheniramine, clomipramine, dexamethasone, dextromethorphan, dextromethorphan/phenylephrine, diclofenac, diphenhydramine, diphenhydramine/phenylephrine, donepezil, dronabinol, epinephrine, escitalopram, famotidine, fentanyl, glimepiride, GLP-1 peptides, granisetron, insulin, insulin nanoparticles, insulin/GLP-1 nanoparticles, ketamine, ketoprofen, ketotifen, caffeine, levocetirizine, loperamide, loratadine, meclizine, methylphenidate, midazolam, mirodenafil, montelukast, multimeric-001, naloxone, nicotine, nitroglycerin, olanzapine, olopatadine, ondansetron, oxybutynin, pectin, pectin/menthol, pectin/ascorbic acid, PediaSUNAT (artesunate and amodiaquine), piroxicam, phenylephrine, prednisolone, pseudoephedrine, risperidone, rivastigmine, rizatriptan, selegiline, *Senna* glycosides, sildenafil citrate, simethicone, sumatriptan, tadalafil, testosterone, triamcinolone acetonide, triptan, tropicamide, voglibose, zolmitriptan, zolpidem, or pharmaceutically acceptable salts of these compounds. The active pharmaceutical ingredient can also be present in the form of a mixture of different active ingredients. As non-active pharmaceutical ingredient, the administration form according to the invention can contain, for example, active ingredients for oral hygiene, such as menthol.

The at least one active pharmaceutical ingredient is preferably contained in the film in a constant concentration and in this regard has a uniformity of the active ingredient content ("content uniformity") of from 85 to 115% of the target content, preferably 90 to 110% of the target content, and especially preferably 95 to 105% of the target content, in relation to the area of a unit dose of the film (prior to rolling up).

The active ingredient content per dosing unit of a rolled-up film produced by the method according to the invention is up to 500 mg, preferably up to 250 mg, especially preferably up to 230 mg, more preferably up to 200 mg, and even more preferably up to 100 mg. On the other hand, the minimum active ingredient content per dosing unit can preferably be 5 mg, more preferably 10 mg, and most preferably 12 mg. Depending on the application, the active ingredient content may also lie in the upper range of the above values, for example in the range of more than 50 to 100 mg or 30 to 50 mg.

The amount of active ingredient relative to the area of the administration form according to the invention before rolling up is expediently in the range of from 1 to 15 mg/cm², and preferably 2.8 to 10 mg/cm².

The film according to the invention, which is suitable as a film-administering form, can contain, besides the aforementioned film-forming polymer, further ingredients, especially excipients, which are selected from the group comprising colouring agents, aromatic substances, especially flavourings and/or odorants, sweeteners, taste-masking agents, surfactants, enhancers, pH regulators, preservatives and/or antioxidants. The addition of flavourings, odorants and aromatic substances is especially advantageous, individually or in combination. A suitable taste-masking agent is, for example, an ion exchange resin. The film suitable as a film-administering form preferably contains flavourings, odorants and aromatic substances, individually or in combination.

In addition, the film suitable as an oral film-administering form can contain a pigment or a UV-absorbing agent which protects a light-sensitive active ingredient introduced into the film against UV light.

Besides the auxiliaries mentioned above, the film suitable as an oral film-administering form can also additionally contain constituents for optimising its flexibility and/or physical properties, such as a plasticiser and/or a humectant. Preferred plasticisers and/or humectants in the context of the present invention are, for example, selected from the group comprising glycerol, propylene glycol, polyethylene glycol and citric acid ester. Glycerol is very especially preferably used as plasticiser.

The film suitable as a film-administering form can be embodied as a more solid film (without gas inclusions) or as a solidified foam. If the film suitable as a film-administering form is present as a solidified foam, an introduced gas, such as air, nitrogen or $CO_2$, or another gas can be contained.

Suitable basic materials and methods for producing corresponding solidified foam formulations are described for example in EP 1 296 661 A2, EP 1 959 921 A2 or WO 2018/224591 A1.

If the film-administering form is embodied as a solidified foam, the voids of the foam can be present isolated from one another in the polymer matrix, preferably in the form of solidified bubbles.

According to another embodiment, it is provided that the voids are connected to one another, preferably by forming a continuous channel system penetrating the matrix.

If the film-administering form is embodied as a solidified foam, the voids of the foam expediently have a volume fraction of from 5 to 98%, preferably 30 to 80%, in relation to the total volume of the film (i.e. any self-adhering layers provided are not to be taken into consideration for the volume fraction). In this way, an accelerated dissolution of the film-administering form is influenced favourably.

Another important parameter that influences the properties of the foam-based film-administering form according to the invention is the diameter of the voids or bubbles. The bubbles or voids are preferably created with the aid of a foam whipping machine, with which the diameter of the bubbles can be adjusted in a wide range, almost arbitrarily. The diameter of the bubbles or voids can thus lie in the range of from 0.01 to 60 μm. The diameter especially preferably lies in the range of 10 and 50 μm.

The thickness of the film layer of the film suitable as an oral film-administering form preferably lies in the range of from approximately 0.01 to approximately 2 mm, and especially preferably in the range of from 0.02 to approximately 1 mm.

In respect of the material from which the self-adhering layer is formed, the present invention is also not subject to any relevant limitations, on the proviso that the self-adhering layer should be based on a pharmaceutically acceptable water-soluble or water-dispersible polymer. A suitable water-soluble or water-dispersible polymer is for example Plastoid E35H (softened Eudragit E100; lauric acid, adipic acid and glycerol are added as modifiers). Further suitable water-soluble or water-dispersible polymers are, for example, shellac, a vinylpyrrolidone/vinyl acetate copolymer, a polyvinylcaprolactam/polyvinyl acetate/polyethylene glycol copolymer, hydroxypropylcellulose or hydroxypropyl methylcellulose and/or polyvinylpyrrolidone. A water-soluble polymer that is very especially preferred within the scope of the present invention is polyvinylpyrrolidone.

The aforementioned water-soluble polymers are expediently combined with a plasticiser. Examples of suitable plasticisers are, for example, glycerol, polyethylene glycol, especially polyethylene glycol 200, sorbitol and/or tributyl citrate, of which glycerol, polyethylene glycol 200 and/or tributyl citrate can be described as especially suitable. A very especially suitable plasticiser is glycerol.

With regard to the ratio of water-soluble polymer to plasticiser, the adhesive is not subject to any relevant limitations, provided the ratio is set such that the mixture is sufficiently tacky and workable. An example of a favourable mixing ratio can be a ratio of water-soluble polymer to plasticiser of approximately 85 to 50 to approximately 15 to 50, preferably from approximately 85 to 65 to approximately 15 to 35, even more preferably from approximately 80 to 60 to approximately 20 to 40, even more preferably from approximately 80 to 50 to approximately 20 to 50, even more preferably from approximately 82 to 68 to approximately 18 to 32 and most preferably from approximately 80 to 70 to approximately 20 to 30.

A suitable proportion of the water-soluble or water-dispersible polymer in the self-adhering layer can be specified as a proportion of from approximately 50 to 90 and preferably from approximately 60 to 85% in the film.

With this type of activation of the (first) surface of the film produced in step (a), an intermediate layer—even if only relatively extremely thin—remains, after the rolling up, between the activated (first) surface and the non-activated (second) surface of the film in the rolled-up laminate, i.e. the layer thickness of the self-adhering layer is preferably smaller than the layer thickness of the active-ingredient-containing film of the film-administering form, at least by a factor of 2, more preferably at least by a factor of 4, and even more preferably at least by a factor of 8.

The activated film can expediently be rolled up by means of rotating brushes at an angle of approximately 45°. It is additionally possible to attach a winding core to the laminate provided in flat form and to then wind up the laminate onto this winding core. After completion, the winding core can be removed, so that a central hollow is created. This can have a diameter of from approximately 0.5 to 30 mm, preferably from approximately 1 to 10 mm, and especially preferably from approximately 2 to 5 mm.

Alternatively, it is possible that the winding core remains in the system as part of the preparation, wherein this winding core can be compact or hollow, provided in the present case as a ring, containing an active ingredient or largely free from active ingredients. In addition, the width of the winding core may exceed the maximum width of the laminate. The diameter of the winding core is expediently approximately 0.5 to 30 mm, preferably approximately 1 to 10 mm, and especially preferably approximately 2 to 5 mm.

The rolled-up laminate can be divided, after the rolling up in step (c), into smaller individual portions. For this purpose, the method according to the invention expediently contains a step of cutting of the rolled-up laminate produced in (c). Portions of such laminate rolls with a constant width, for example of from 1 to 4 cm, and especially 1.5 to 2.5 cm, are thus created.

Figure 2:
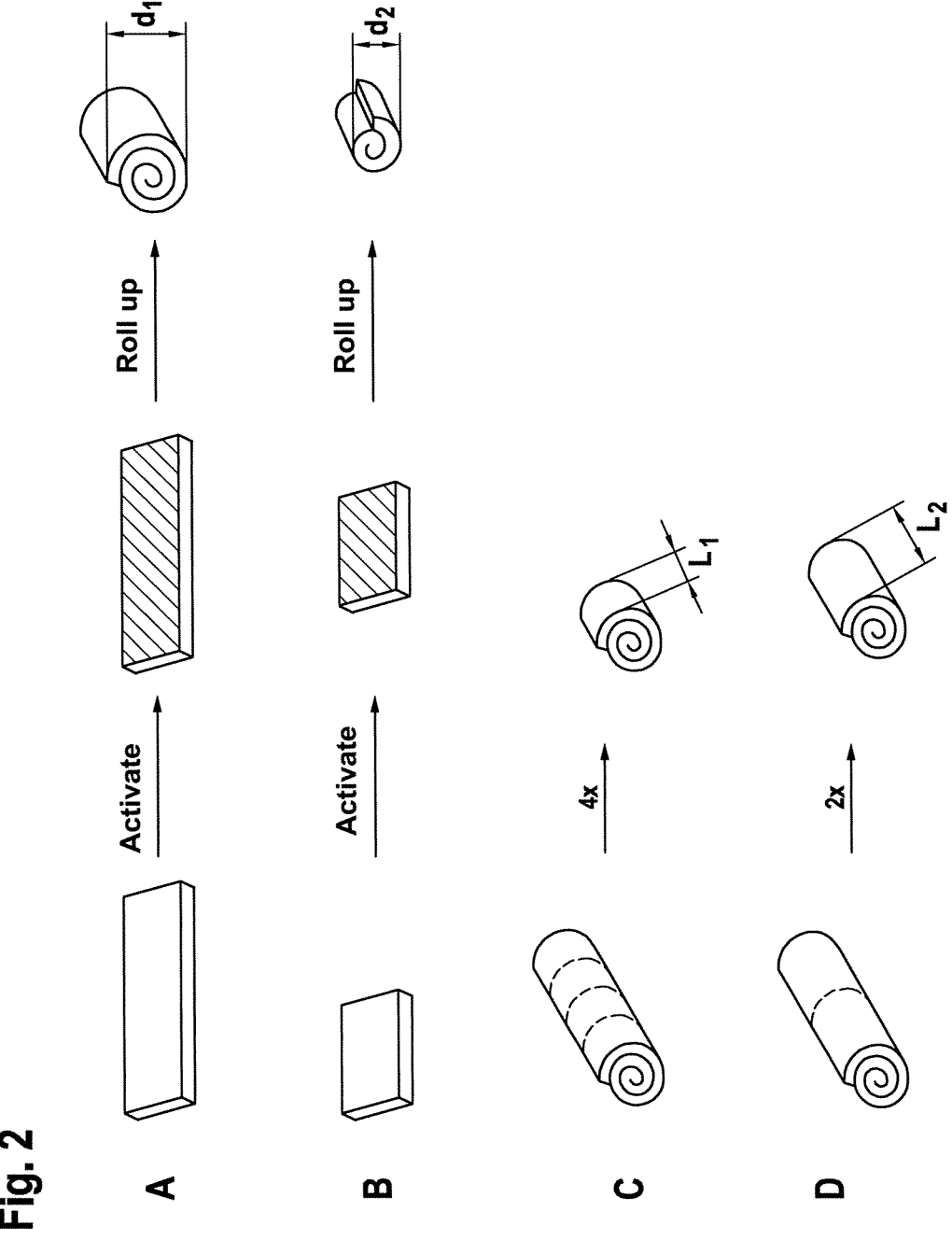

The flexibility in the production of different shapes and sizes of the rolled-up laminates according to the invention is illustrated in FIG. 2. In FIG. 2A a relatively long film is activated in a first step on a surface and is then rolled up, wherein a relatively thick rolled-up laminate is obtained (d1). In FIG. 2B a shorter film is activated on a surface and is then rolled up, wherein a thinner rolled-up laminate is obtained (d2<d1).

In FIGS. 2C and 2D the flexibility on the basis of the adjustable length of the rolled-up laminates is illustrated, by means of which, for example, the desired active ingredient amount can be adapted to the needs of the individual patient on the basis of an active ingredient film with active ingredient concentration predetermined by the manufacturer. A pre-rolled-up film laminate can be cut for example into 4 equal parts (C) or into 2 equal parts (D), wherein film laminate pieces of different length ($L_2=2\ L_1$) are obtained.

According to a second aspect, the present invention relates to a rolled-up laminate which can be produced or is produced by the method described above. The rolled-up laminate preferably has a weight of from approximately 100 to 1000 mg, and preferably approximately 200 to 800 mg.

Furthermore preferred for the rolled-up laminate according to the invention is a residual solvent or residual water content of less than 10 wt. %, and especially less than 5 wt. %.

For the rolled-up laminate according to the invention it is essential that it consists substantially (i.e. to an extent of more than 95 wt. % and preferably to an extent of more than 98 wt. %) and preferably completely of water-soluble or water-dispersible constituents, so that the laminate dissolves or disintegrates relatively quickly upon contact with water and releases the active ingredient incorporated in it. To this end, both the active-ingredient-containing layer and any self-adhering layer present expediently have a dissolution rate (determined for the individual film in accordance with adapted test A for the disintegration time of capsules and tablets, European Pharmacopoeia (2011), wherein the layer in question is directly secured to the shaft of the disintegration tester) of less than approximately 5 min, preferably less than approximately 120 s, and more preferably less than approximately 50 s. If the rolled-up laminate according to the invention contains an ion exchanger as taste-masking agent, this is understood in the context of this invention to be a water-soluble or water-dispersible constituent.

The rolled-up laminate according to the invention is suitable especially for oral administration, including buccal, gingival or sublingual administration, of active ingredients or administration on the palate.

The rolled-up laminate can be modified in many ways. For example, it can be filled into a capsule, which can then be swallowed. Alternatively, the rolled-up laminate can be modified with a coating that is soluble in gastric juices, intended for dissolution in the stomach, or with a coating that is resistant to gastric juices, intended for dissolution in the intestine. Due to the rolled-up form, an application in all body openings (for example in the mouth, in the nostrils, ear canals, anus, vagina) is possible without difficulty. In addition, the rolled-up material can be dispensed in a dispenser as required, and cut. Due to the roll form, the material can also be applied well in the cheek pouch or under the tongue, without disturbance. Due to the dissolution, a very high area density of >100 mg/cm (with a diameter of 0.5 mm, for example) can be achieved. Additionally, relatively long pieces can be applied (<3 cm, i.e., more than 300 mg).

In the following, the present invention will be illustrated in greater detail on the basis of a practical example which, however, should not be regarded as limiting the scope of protection of the application in any way.

Example 1

A foamed film was produced with the composition specified in the table below for the active ingredient layer (layer thickness: ~0.4 mm; area density 200 g/m²).

| Material | Function | Proportion [% dry] |
|---|---|---|
| Adhesive layer | | |
| PVP VA64 | Polymer | 80 |
| Glycerol | Plasticiser | 20 |
| Active ingredient layer | | |
| Polyvinyl alcohol[1] | Polymer | 77.6 |
| FD&C Red 40 | Colouring agent | 0.4 |
| Saccharin Na | Sweetener | 2.0 |
| Sucralose | Sweetener | 4.0 |
| Glycerol | Plasticiser/humectant | 9.0 |
| Cherry Flavour | Flavouring | 6.0 |
| Menthol | Flavouring | 1.0 |

[1]= 35% in water

For the production, the further ingredients were stirred into a PVA pre-solution and set to a solids content of 34.5% under further stirring with water. The resultant mixture was then homogenised for 2 h, foamed using a foaming machine, and processed using a roll coater to form a foam film. The residual solvent content of the dried film was approximately 3%.

The adhesive layer formed of PVP VA64 and glycerol was applied to this film by transfer from a dehesively finished carrier. The laminate thus produced was rolled up with adhesive layer on the inner side and cut into portions.

The invention claimed is:

1. A method for producing a water-soluble or water-dispersible active-ingredient-administering form comprising
   (a) producing a film, suitable as oral film-administering form, having a content of active ingredient, wherein the film-administering form is present as a solid foam,
   (b) activating a surface of the film produced in (a) in order to generate a tacky surface, and
   (c) rolling up the film activated in (b) to form a rolled-up laminate.

2. The method according to claim 1, characterised in that the surface is activated and a tacky surface is generated by swelling, etching or melting of the surface.

3. The method according to claim 1, characterised in that the surface is activated and a tacky surface is generated by applying a self-adhering layer, wherein the self-adhering layer is formed from a water-erodible material and preferably a water-soluble or water-dispersible material.

4. The method according to claim 1, characterised in that the film suitable as an oral film-administering film is based on a film-forming polymer, selected from polyvinyl alcohol, polyethylene glycol, polyethylene oxide, cellulose derivatives, pullulan, gelatines, and agar.

5. The method according to claim 4, characterised in that the film-forming polymer accounts for a proportion of from 25 to 85 wt. % in the film.

6. The method according to claim 1, characterised in that the film suitable as oral film-administering form contains at least one excipient selected from flavourings or aromatic substances, colouring agents, plasticisers and sweeteners.

7. The method according to claim 1, characterised in that the active ingredient is an active pharmaceutical ingredient selected from the group comprising acetaminophen, adrenaline, alprazolam, amlodipine, anastrozole, apomorphine, aripiprazole, atorvastatin, baclofen, benzocaine, benzocaine/ menthol, benzydamine, buprenorphine, buprenorphine/ naloxone, buprenorphine/naloxone/cetirizine, cetirizine, chlorpheniramine, clomipramine, dexamethasone, dextromethorphan, dextromethorphan/phenylephrine, diclofenac, diphenhydramine, diphenhydramine/phenyleph-rine, donepezil, dronabinol, epinephrine, escitalopram, famotidine, fentanyl, glimepiride, GLP-1 peptides, granis-etron, insulin, insulin nanoparticles, insulin/GLP-1 nanopar-ticles, ketamine, ketoprofen, ketotifen, caffeine, levocetiriz-ine, loperamide, loratadine, meclizine, methylphenidate, midazolam, mirodenafil, montelukast, multimeric-001, naloxone, nicotine, nitroglycerin, olanzapine, olopatadine, ondansetron, oxybutynin, pectin, pectin/menthol, pectin/ ascorbic acid, PediaSUNAT (artesunate and amodiaquine), piroxicam, phenylephrine, prednisolone, pseudoephedrine, risperidone, rivastigmine, rizatriptan, selegiline, *Senna* gly-cosides, sildenafil citrate, simethicone, sumatriptan, tadala-fil, testosterone, triamcinolone acetonide, triptan, tropic-amide, voglibose, zolmitriptan, zolpidem, or pharmaceutically acceptable salts of these compounds.

8. The method according to claim 3, characterised in that the self-adhering layer is based on a water-soluble or water-dispersible polymer.

9. The method according to claim 8, characterised in that the water-soluble or water-dispersible polymer accounts for a proportion of from 50 to 90 wt. % in the self-adhering layer.

10. The method according to claim 1, characterised in that the film suitable as oral film-administering form or the self-adhering film contains a plasticiser and/or a humectant.

11. A rolled-up laminate, producible by a method accord-ing to claim 1.

12. The rolled-up laminate according to claim 11, char-acterised in that it has a weight of from 100 to 1000 mg.

13. The method according to claim 1, characterised in that the film suitable as an oral film-administering film is based on polyvinyl alcohol.

14. The method according to claim 4, characterised in that the film-forming polymer accounts for a proportion of from 60 to 80 wt. % in the film.

15. The method according to claim 3, characterised in that the self-adhering layer is based on polyvinylpyrrolidone.

16. The method according to claim 8, characterised in that the water-soluble or water-dispersible polymer accounts for a proportion of from 60 to 85 wt. % in the self-adhering layer.

17. The method according to claim 1, characterised in that the film suitable as oral film-administering form or the self-adhering film contains a glycerol.

18. The rolled-up laminate according to claim 11, char-acterised in that it has a weight of from 200 to 800 mg.

* * * * *